DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 21, 1971

890 O.G. 980

T890,005

SYNTHESIS OF 1,12-DODECANEDIOIC ACID TO REDUCE LEVEL OF MONOBASIC ACID IMPURITIES

John Ejnar Fallon, Wilmington, Del., and Thomas Whitfield Wilson, Glassboro, N.J., assignors to E. I. du Pont de Nemours and Company, Wilmington, Del.

Continuation of application Ser. No. 569,815, Aug. 3, 1966. This application June 12, 1970, Ser. No. 45,943

Int. Cl. C07c *55/04*

U.S. Cl. 260—533C

No Drawing. 10 Pages Specification

In a process for the oxidation of cyclododecane to 1,12-dodecanedioic acid comprising the steps of oxidizing cyclododecane with oxygen to an initial oxidate mixture comprising cyclododecanol and cyclododecanone, distilling to remove volatile materials including by-products and uncovered cyclododecane from the mixture, oxidizing the resulting cyclododecanol/cyclododecanone mixture with nitric acid to form 1,12-dodecanedioic acid, and recovering 1,12-dodecanedioic acid, the additional step of washing the initial oxidate with an aqueous solution of sodium hydroxide, potassium hydroxide, ammonium hydroxide, or calcium hydroxide at a temperature in the range of 120–230° C. to reduce the amount of monobasic acid impurities therein, said additional step being conducted between the steps of oxidizing cyclododecane with oxygen and oxidizing the cyclododecanol/cyclododecanone mixture with nitric acid, i.e., either before or after the distillation step.